(12) United States Patent
    Garner

(10) Patent No.: US 12,557,980 B2
(45) Date of Patent: Feb. 24, 2026

(54) INFLATABLE SPECULUM DEVICE

(71) Applicant: Elizabeth Garner, Montclair, NJ (US)

(72) Inventor: Elizabeth Garner, Montclair, NJ (US)

( * ) Notice: Subject to any disclaimer, the term of this patent is extended or adjusted under 35 U.S.C. 154(b) by 41 days.

(21) Appl. No.: 18/619,475

(22) Filed: Mar. 28, 2024

(65) Prior Publication Data

US 2025/0302292 A1    Oct. 2, 2025

(51) Int. Cl.
    *A61B 1/32*        (2006.01)
    *A61B 1/303*       (2006.01)
    *A61M 29/02*       (2006.01)

(52) U.S. Cl.
    CPC ............... *A61B 1/32* (2013.01); *A61B 1/303* (2013.01); *A61M 29/02* (2013.01)

(58) Field of Classification Search
    CPC ....... A61B 1/303; A61B 1/32; A61B 1/00082; A61M 29/02
    USPC .................................. 600/184–186, 201–246
    See application file for complete search history.

(56) References Cited

U.S. PATENT DOCUMENTS

| | | | |
|---|---|---|---|
| D274,356 S | | 6/1984 | Riedell |
| 5,716,329 A | * | 2/1998 | Dieter .................... A61B 1/303 |
| | | | 600/184 |
| 5,730,748 A | * | 3/1998 | Fogarty ............ A61B 17/00008 |
| | | | 600/207 |
| 5,743,852 A | | 4/1998 | Johnson |
| 5,865,729 A | * | 2/1999 | Meehan .................. A61B 17/42 |
| | | | 600/245 |
| 7,041,056 B2 | | 5/2006 | Deslauriers |
| 2010/0016674 A1 | | 1/2010 | Mills |
| 2012/0059225 A1 | * | 3/2012 | Gostout ............. A61B 17/0218 |
| | | | 600/204 |
| 2017/0014161 A1 | * | 1/2017 | Gemmer ............... A61M 29/00 |
| 2017/0303903 A1 | * | 10/2017 | De Koning ........ A61B 1/00103 |
| 2018/0071502 A1 | * | 3/2018 | Hakim ...................... A61F 2/82 |
| 2020/0046216 A1 | * | 2/2020 | Moein .................... A61B 1/303 |

FOREIGN PATENT DOCUMENTS

| | | | |
|---|---|---|---|
| CA | 2242738 | 7/1997 | |
| CN | 105828865 A | * 2/2021 | ......... A61B 17/1204 |

* cited by examiner

*Primary Examiner* — Jessica Weiss

(57)                ABSTRACT

An inflatable speculum device for more comfortably and conveniently expanding the vaginal cavity to facilitate visualization of the cervix includes a tube having an interior space. The tube is made of a resiliently deformable material wherein the tube is configured to inflate. A hose is couplable to the tube and is in environmental communication with the interior space of the tube. A pump is fluidly coupled to the hose wherein activation of the pump moves air into the interior space of the tube through the hose thereby inflating the tube. The tube fits within a body cavity of a user whereby the tube is configured to dilate the body cavity when the tube inflates.

15 Claims, 8 Drawing Sheets

INFLATABLE SPECULUM DEVICE

CROSS-REFERENCE TO RELATED APPLICATIONS

Not Applicable

STATEMENT REGARDING FEDERALLY SPONSORED RESEARCH OR DEVELOPMENT

Not Applicable

THE NAMES OF THE PARTIES TO A JOINT RESEARCH AGREEMENT

Not Applicable

INCORPORATION-BY-REFERENCE OF MATERIAL SUBMITTED ON A COMPACT DISC OR AS A TEXT FILE VIA THE OFFICE ELECTRONIC FILING SYSTEM

Not Applicable

STATEMENT REGARDING PRIOR DISCLOSURES BY THE INVENTOR OR JOINT INVENTOR

Not Applicable

BACKGROUND OF THE INVENTION

(1) Field of the Invention

The disclosure relates to vaginal speculums and more particularly pertains to a new vaginal speculum for more comfortably and conveniently expanding the vaginal cavity to facilitate visualization of the cervix.

(2) Description of Related Art Including Information Disclosed Under 37 CFR 1.97 and 1.98

The prior art relates to vaginal speculums. Speculums are used to expand the vaginal cavity and other hollow parts of the body for numerous medical procedures, including pap smears, pelvic exams, testing, and insertion of intrauterine devices. Typical speculums are metal or plastic devices with two arms that meet at a hinge. The arms are often shaped like a duck's bill. These speculums expand the body cavity when the arms open, or separate. Speculums are available in a range of standard sizes, in an attempt to make the medical procedures more comfortable. However, the use of speculums remains uncomfortable, and sometimes even painful. Thus, there is a need in the art for a speculum device that is more comfortable for the patient and that will facilitate visualization of body cavities for medical professionals.

BRIEF SUMMARY OF THE INVENTION

An embodiment of the disclosure meets the needs presented above by generally comprising a tube having an interior space. The tube comprises a resiliently deformable material wherein the tube is configured to inflate. A hose is couplable to the tube and is in environmental communication with the interior space of the tube. A pump is fluidly coupled to the hose wherein activation of the pump moves air into the interior space of the tube through the hose thereby inflating the tube. The tube is configured to fit within a body cavity of a user whereby the tube is configured to dilate the body cavity when the tube inflates.

There has thus been outlined, rather broadly, the more important features of the disclosure in order that the detailed description thereof that follows may be better understood, and in order that the present contribution to the art may be better appreciated. There are additional features of the disclosure that will be described hereinafter and which will form the subject matter of the claims appended hereto.

The objects of the disclosure, along with the various features of novelty which characterize the disclosure, are pointed out with particularity in the claims annexed to and forming a part of this disclosure.

BRIEF DESCRIPTION OF SEVERAL VIEWS OF THE DRAWING(S)

The disclosure will be better understood and objects other than those set forth above will become apparent when consideration is given to the following detailed description thereof. Such description makes reference to the annexed drawings wherein.

DETAILED DESCRIPTION OF THE INVENTION

Figure 1:
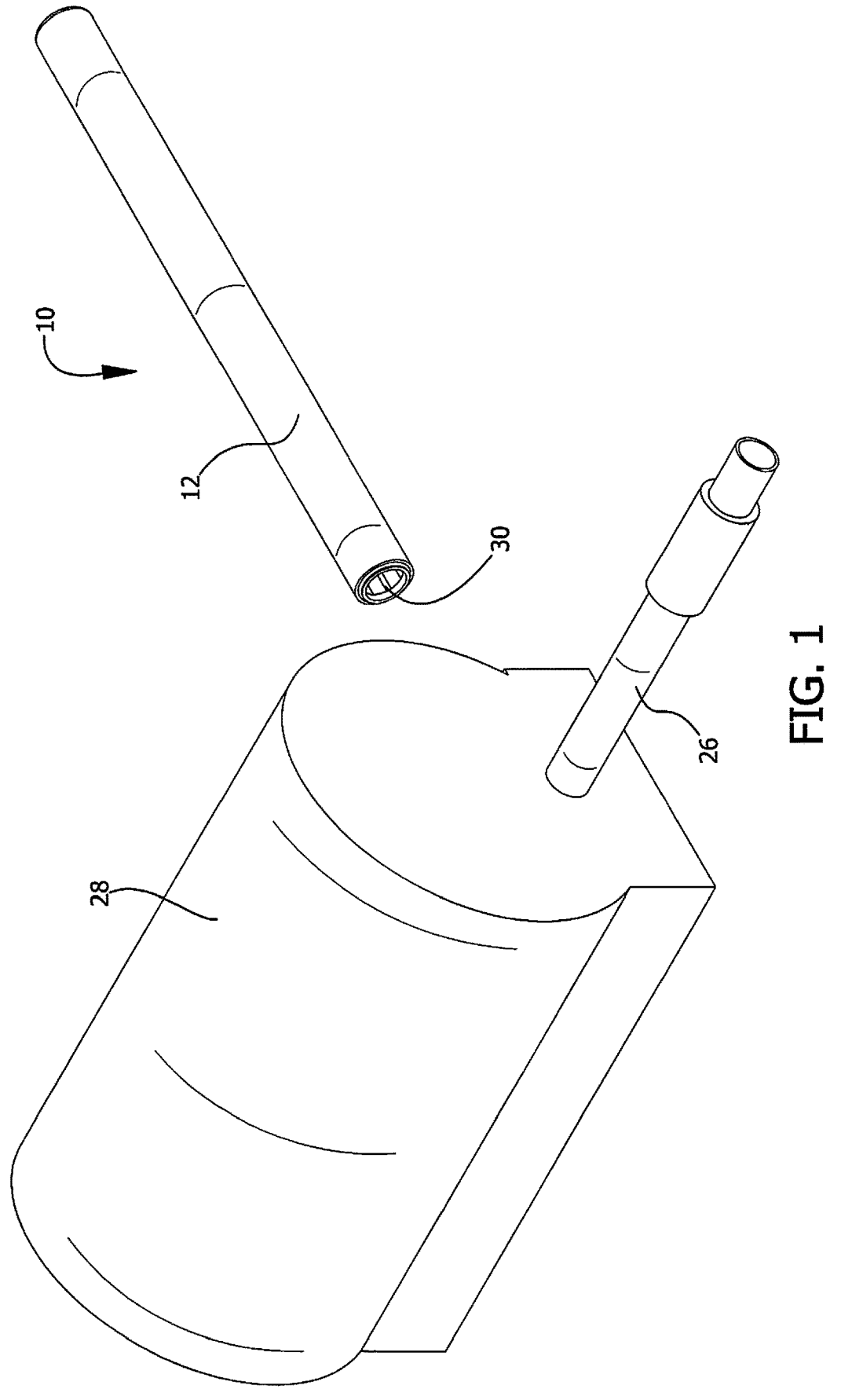
FIG. 1 is an isometric view of an inflatable speculum device according to an embodiment of the disclosure.
Figure 2:
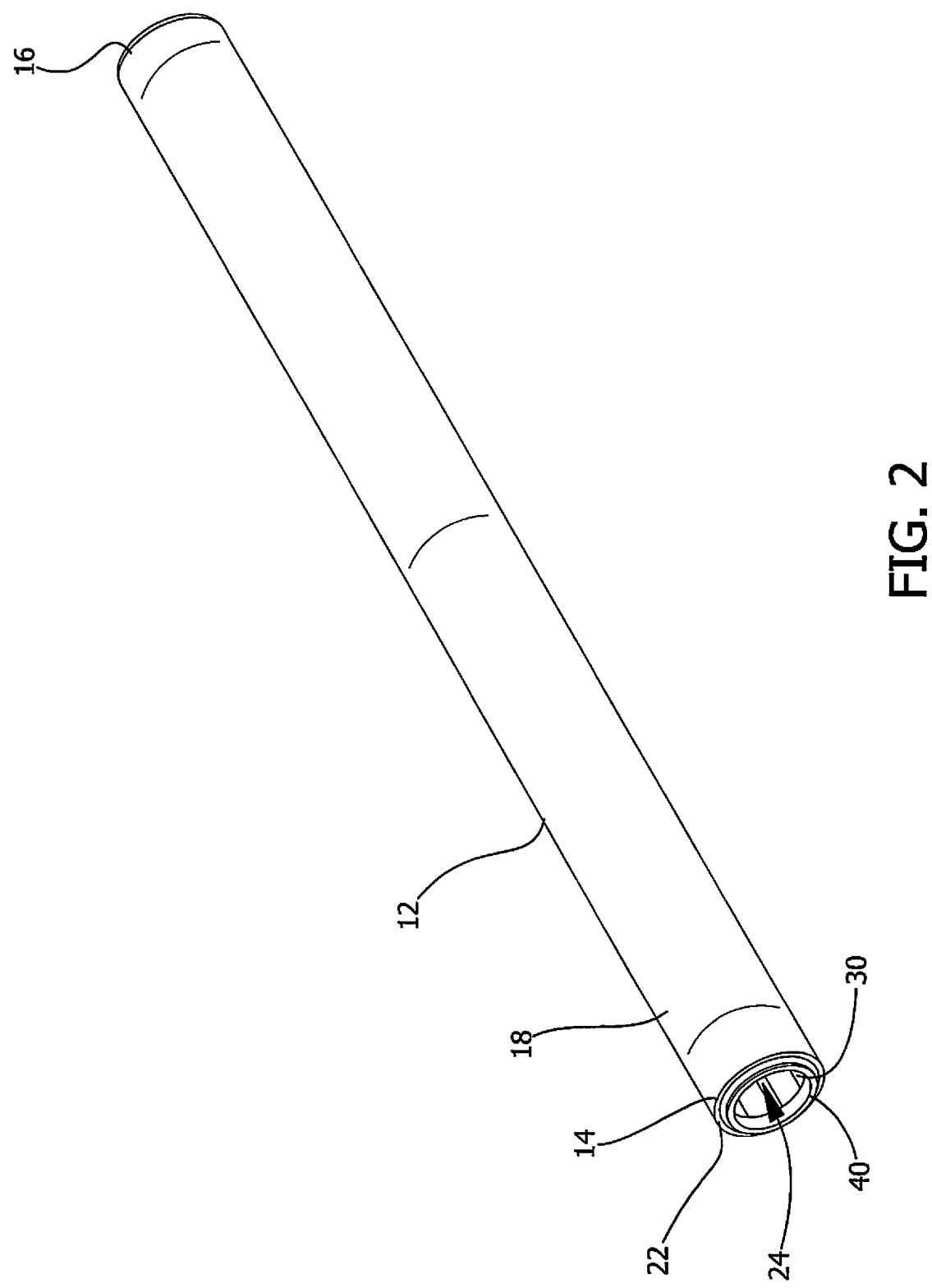
FIG. 2 is an isometric view of an embodiment of the disclosure.
Figure 3:
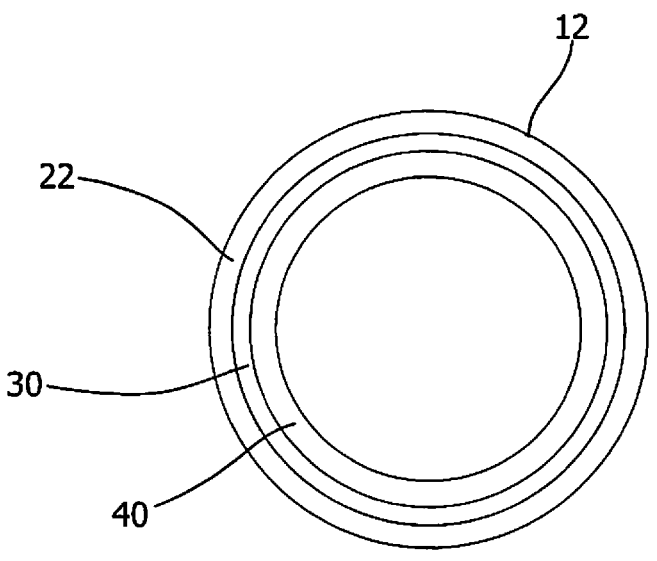
FIG. 3 is a rear view of an embodiment of the disclosure.
Figure 4:
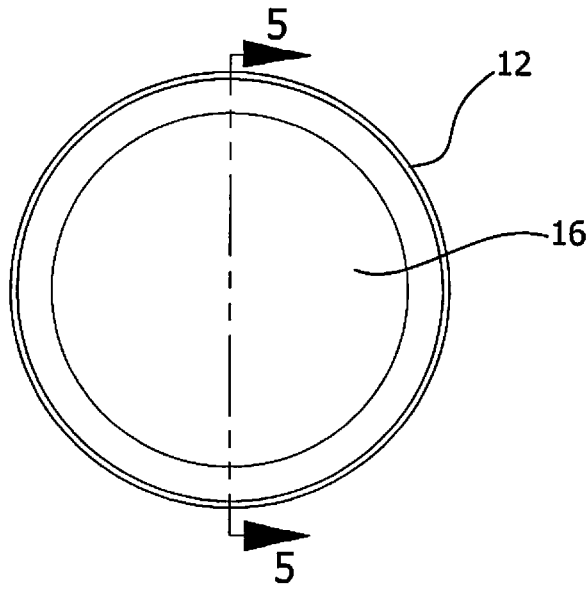
FIG. 4 is a front view of an embodiment of the disclosure.
Figure 5:
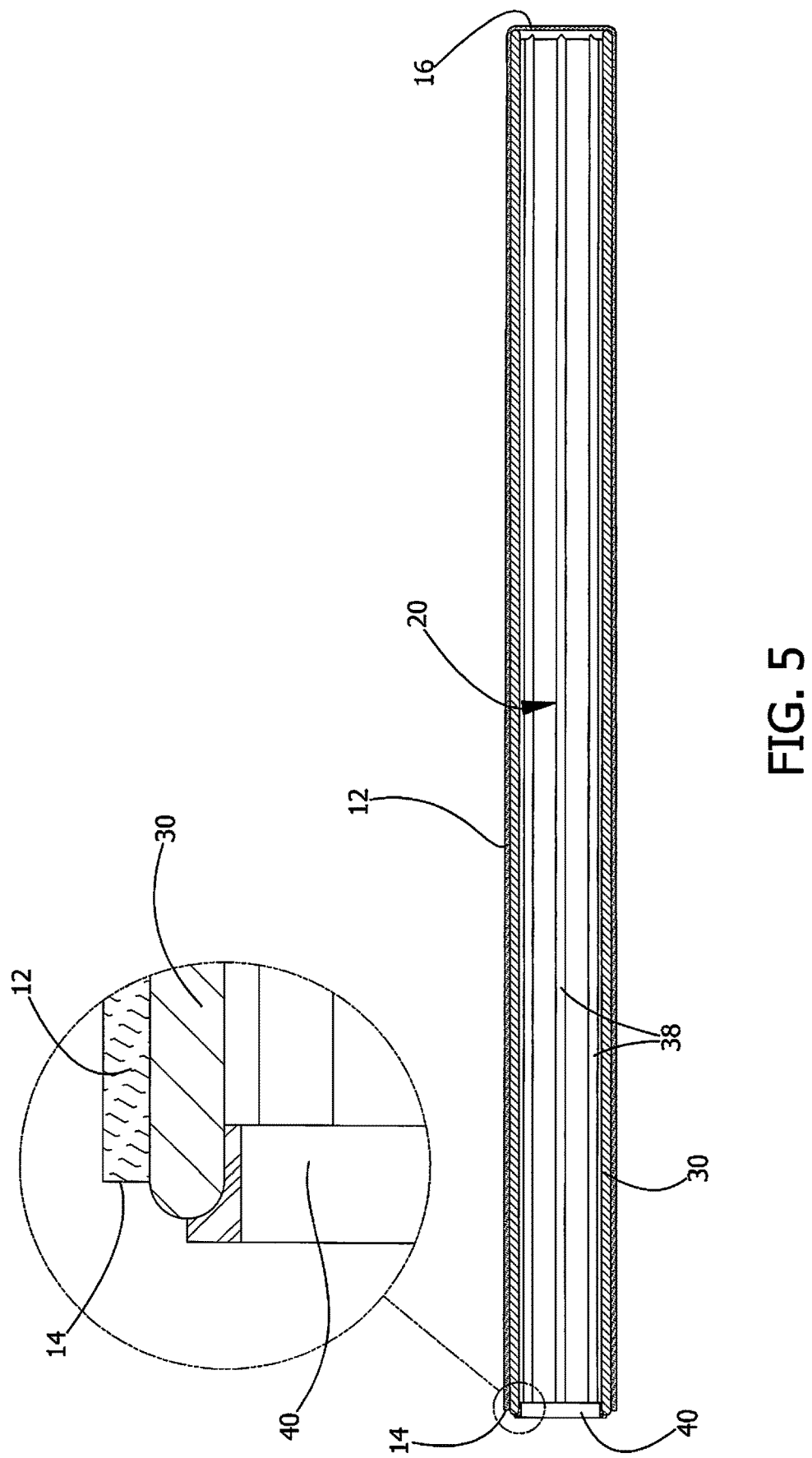
FIG. 5 is a cross-sectional view of an embodiment of the disclosure.
Figure 6:
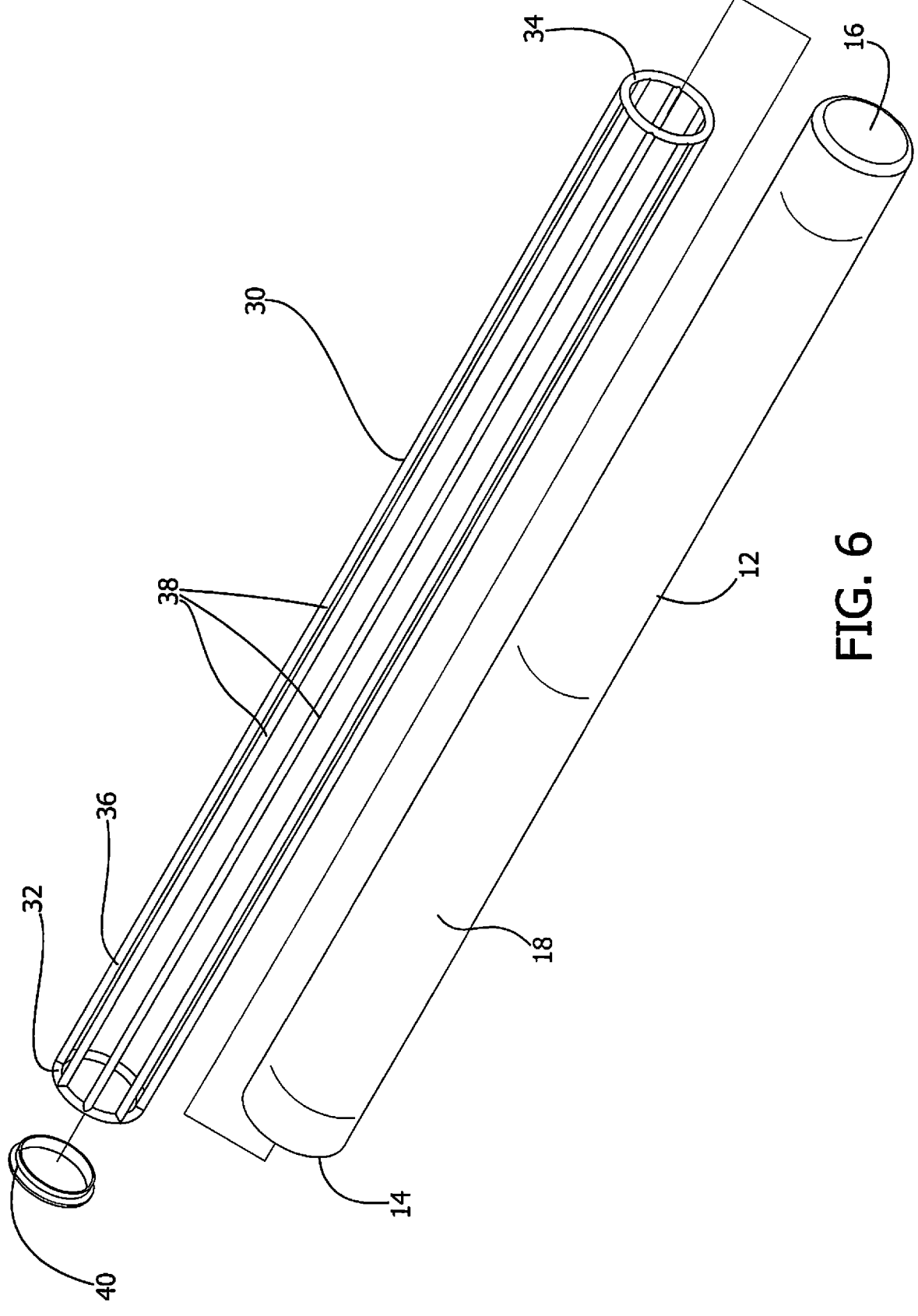
FIG. 6 is an exploded view of an embodiment of the disclosure.

With reference now to the drawings, and in particular to FIGS. 1 through 9 thereof, a new vaginal speculum embodying the principles and concepts of an embodiment of the disclosure and generally designated by the reference numeral 10 will be described.

As best illustrated in FIGS. 1 through 9, the inflatable speculum device 10 generally comprises a tube 12 having a first end 14, a second end 16, and a tube body 18 that is coupled to and extends between the first end 14 and the second end 16 to define an interior space 20. The tube body 18 may be elongated. The first end 14 may have a tube edge 22 defining an opening 24 into the interior space 20. The second end 16 is generally closed. The tube 12 comprises a resiliently deformable material wherein the tube 12 is configured to be inflatable.

A hose 26 is couplable to the tube 12, for example being couplable to the first end 14 of the tube 12. The hose 26 is in environmental communication with the interior space 20 of the tube 12 when the hose 26 is coupled to the tube 12.

A pump 28 is fluidly coupled to the hose 26. Activation of the pump 28 moves air into the interior space 20 of the tube 12 through the hose 26 when the hose 26 is coupled to the tube 12 thereby inflating the tube 12. In some embodiments, the pump 28 may be a manual, hand-held pump, such as a rubber bulb or diaphragm pump. Alternatively, the pump 28 may be an automatic or machine-operated pump.

Figure 7:
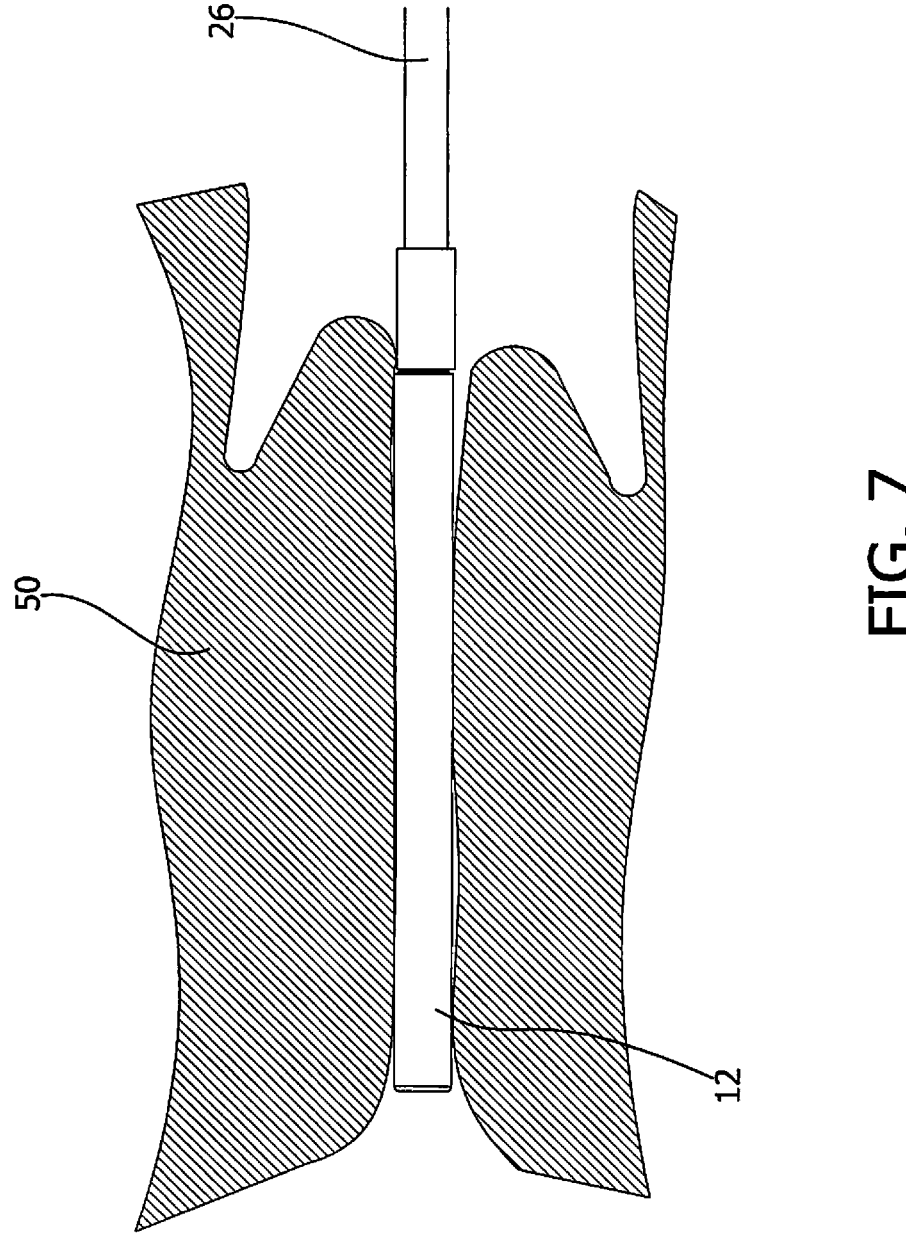
FIG. 7 is an in-use view of an embodiment of the disclosure.
Figure 8:
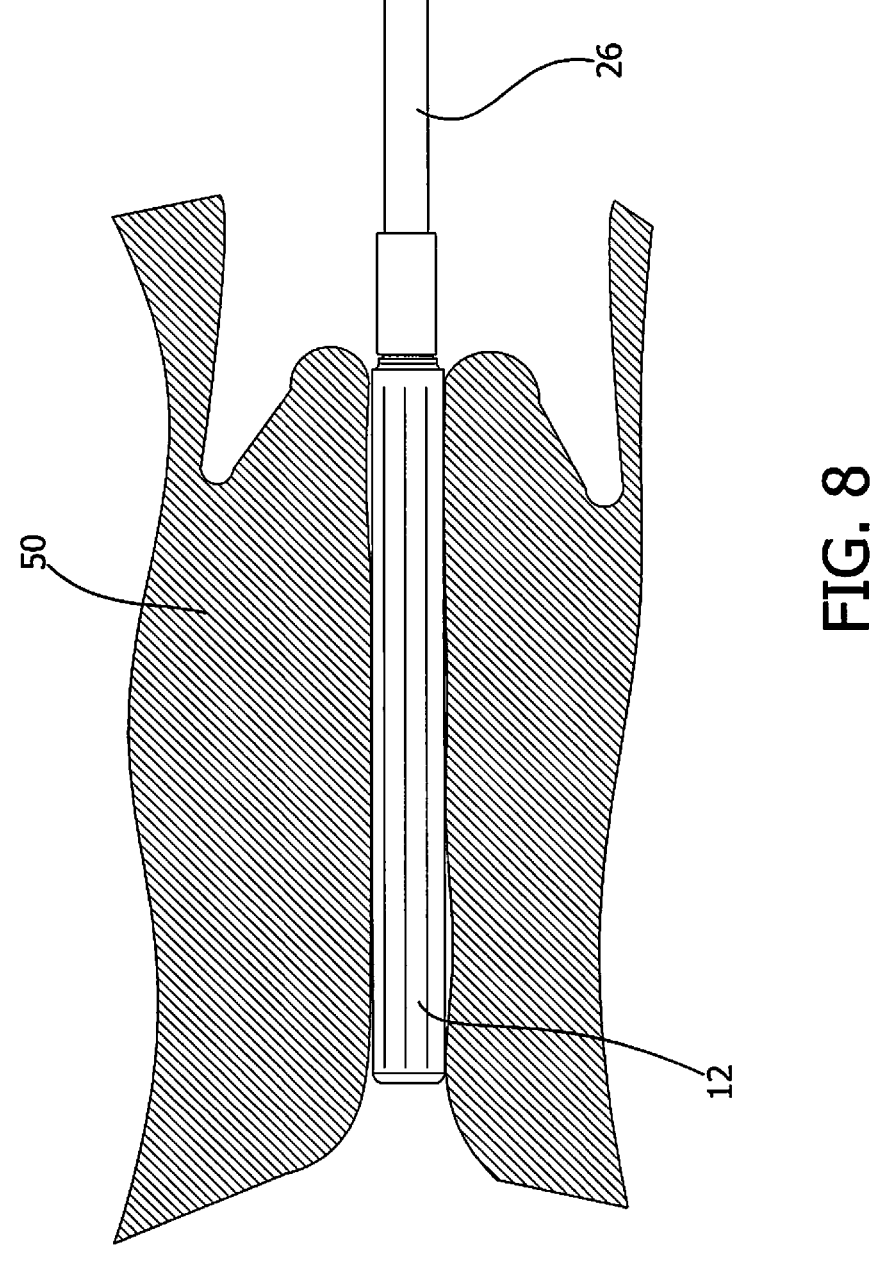
FIG. 8 is an in-use view of an embodiment of the disclosure.
Figure 9:
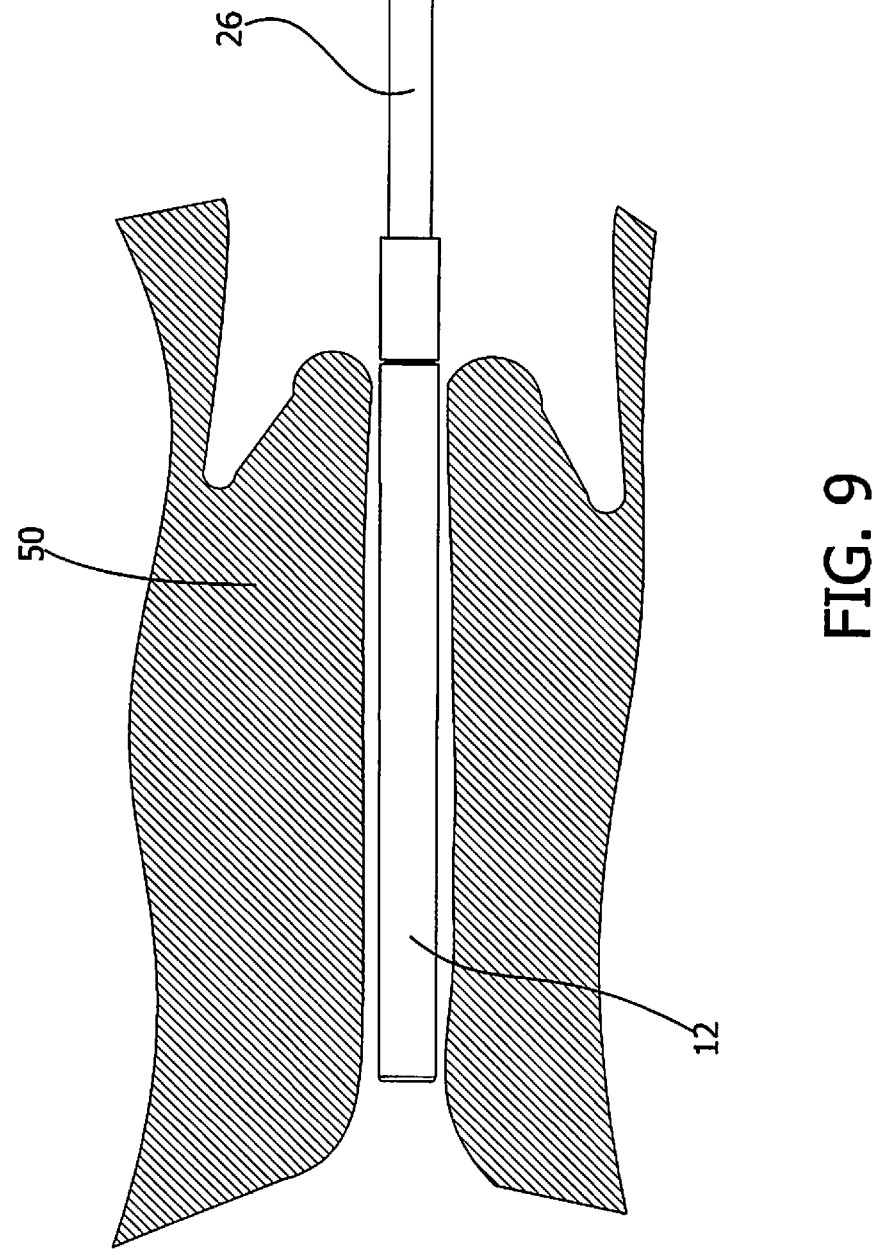
FIG. 9 is an in-use view of an embodiment of the disclosure.

The tube 12 is configured to fit within a body cavity 50 of a user. The tube 12 is configured to dilate the body cavity 50 when the tube 12 inflates, as shown in FIGS. 7-9. Generally, a diameter of the tube 12 increases when the tube 12 inflates. For example, the diameter of the tube 12 may be between 0.5 centimeters (or about 0.2 inches) and 1.5 centimeters (or about 0.6 inches) when the tube 12 is deflated. A length of the tube 12 may be between 10.0 centimeters (or about 3.8 inches) and 20.0 centimeters (or about 7.8 inches) and may remain constant when the tube 12 inflates. Different embodiments of the tube 12 may have different dimensions to accommodate differently sized users or body cavities 50.

A frame 30 may be positioned within the interior space 20. The frame 30 has a shape that is complementary to a shape of the tube 12 when the tube 12 is deflated. The frame 30 generally comprises a plastic material wherein the shape of the frame 30 is configured to remain constant when the tube 12 inflates. The plastic material may be rigid to provide rigidity and structure to the tube 12 when the tube is deflated. The frame 30 thereby facilitates insertion of the tube 12 into the body cavity 50.

The frame 30 may generally comprise a primary end 32 that is positioned adjacent to the first end 14 of the tube 12. The primary end 32 may be open. The primary end 32 may be circular. A secondary end 34 of the frame 30 may be positioned adjacent to the second end 16 of the tube 12. The secondary end 34 may be open. The secondary end 34 may be circular. A frame body 36 may be coupled to and extend between the primary end 32 and the secondary end 34. The frame body 36 may be elongated. The frame body 36 may comprise a plurality of thin rods 38 that are coupled to and extend between the primary end 32 and the secondary end 34. Each rod of the plurality of thin rods 38 may be rounded in shape. Each rod of the plurality of thin rods 38 may have a length that is complementary to a length of the tube body 18.

A fastener 40 may couple the frame 30 to the tube 12. For example, the fastener 40 may have a shape that is complementary to a shape of the first end 14 of the tube 12 and the primary end 32 of the frame 30. The fastener 40 may be positionable within the opening 24 to couple the first end 14 with the primary end 32. The fastener 40 comprise a rubber gasket.

In use, the tube 12 may be inserted into the body cavity 50 while the tube 12 is deflated. Once inserted into the body cavity 50, the tube 12 can be inflated using the pump 28 and the hose 26. Inflation of the tube 12 will dilate the body cavity 50. The body cavity 50, such as the vaginal cavity, may remain dilated, or expanded, for a period of time after the tube 12 has been inflated. The tube 12 may remain within the body cavity 50 to facilitate visualization of the cervix or other portion of the body of the user within the body cavity 50. For example, the hose 26 may be removed from the tube 12 enabling a physician or other medical professional to see within the body cavity 50 through the inflated tube 12.

The inflatable speculum device 10 may be disposable. In particular, the tube 12 and the frame 30 may be designed to be thrown away after a single use.

With respect to the above description then, it is to be realized that the optimum dimensional relationships for the parts of an embodiment enabled by the disclosure, to include variations in size, materials, shape, form, function and manner of operation, assembly and use, are deemed readily apparent and obvious to one skilled in the art, and all equivalent relationships to those illustrated in the drawings and described in the specification are intended to be encompassed by an embodiment of the disclosure.

Therefore, the foregoing is considered as illustrative only of the principles of the disclosure. Further, since numerous modifications and changes will readily occur to those skilled in the art, it is not desired to limit the disclosure to the exact construction and operation shown and described, and accordingly, all suitable modifications and equivalents may be resorted to, falling within the scope of the disclosure. In this patent document, the word "comprising" is used in its non-limiting sense to mean that items following the word are included, but items not specifically mentioned are not excluded. A reference to an element by the indefinite article "a" does not exclude the possibility that more than one of the element is present, unless the context clearly requires that there be only one of the elements.

I claim:

1. A speculum assembly comprising:
   a tube having an interior space, the tube comprising a resiliently deformable material wherein the tube is configured to be inflatable;
   a hose being couplable to the tube and being in fluid communication with the interior space of the tube;
   a pump being fluidly coupled to the hose wherein activation of the pump moves air into the interior space of the tube through the hose thereby inflating the tube;
   the tube being configured to fit within a body cavity of a user whereby the tube is configured to dilate the body cavity when the tube inflates;
   the tube comprising a tube body extending between a first end a second end to define the interior space;
   a frame being positioned within the interior space of the tube, the frame comprising:
      a primary end being positioned adjacent to the first end of the tube, the primary end being open,
      a secondary end being positioned adjacent to the second end of the tube, and
      a frame body extending between the primary end and the secondary end, the frame body being elongated, the frame body comprising a plurality of thin rods being coupled to and extending between the primary end and the secondary end, each rod of the plurality of thin rods having a length being complementary to a length of the tube body; and
   a fastener coupling the frame to the tube.

2. The speculum assembly of claim 1, the first end comprising a tube edge defining an opening into the interior space, wherein the second end is closed.

3. The speculum assembly of claim 1, wherein the hose is couplable to the first end of the tube.

4. The speculum assembly of claim 1, wherein the tube body is elongated.

5. The speculum assembly of claim 1, the pump being a hand-held pump.

6. The speculum assembly of claim 1, further comprising a frame being positioned within the interior space of the tube, the frame having a shape being complementary to a shape of the tube when the tube is deflated.

7. The speculum assembly of claim 6, the frame comprising a plastic material wherein the shape of the frame is configured to remain constant when the tube inflates.

8. The speculum assembly of claim 6, the frame further comprising:
   a primary end being positioned adjacent to a first end of the tube;

a secondary end being positioned adjacent to a second end of the tube; and a frame body extending between the primary end and the secondary end.

9. The speculum assembly of claim 8, the frame body comprising a plurality of thin rods being coupled to and extending between the primary end and the secondary end.

10. The speculum assembly of claim 8, wherein the primary end of the frame is open.

11. The speculum assembly of claim 8, wherein each of the primary end and the secondary end of the frame is circular.

12. The speculum assembly of claim 8, wherein the secondary end of the frame is open.

13. The speculum assembly of claim 1, wherein a diameter of the tube increases when the tube inflates.

14. The speculum assembly of claim 1, the fastener further comprising a rubber gasket.

15. A speculum assembly comprising:

a tube, the tube comprising a tube body extending between a first end and a second end to define an interior space, the tube body being elongated, the first end having a tube edge defining an opening into the interior space, the second end being closed, the tube comprising a resiliently deformable material wherein the tube is configured to inflate;

a hose being couplable to first end of the tube and being in fluid communication with the interior space of the tube;

a pump being fluidly coupled to the hose wherein activation of the pump moves air into the interior space of the tube through the hose thereby inflating the tube, the pump being a manual hand-held rubber pump;

a frame being positioned within the interior space, the frame having a shape being complementary to a shape of the tube when the tube is deflated, the frame comprising a plastic material wherein the shape of the frame is configured to remain constant when the tube inflates, the frame comprising:

a primary end being positioned adjacent to the first end of the tube, the primary end being open, the primary end being circular;

a secondary end being positioned adjacent to the second end of the tube, the secondary end being open, the secondary end being circular;

a frame body extending between the primary end and the secondary end, the frame body being elongated, the frame body comprising:

a plurality of thin rods being coupled to and extending between the primary end and the secondary end, each rod of the plurality of thin rods being rounded, each rod of the plurality of thin rods having a length being complementary to a length of the tube body;

wherein a diameter of the tube increases when the tube inflates;

the tube being configured to fit within a body cavity of a user whereby the tube is configured to dilate the body cavity when the tube inflates; and a fastener coupling the frame to the tube, the fastener having a shape being complementary to a shape of the first end of the tube and the primary end of the frame wherein the fastener is positionable within the opening to couple the first end with the primary end, the fastener comprising a rubber gasket.

* * * * *